United States Patent
Phan Le et al.

(10) Patent No.: US 10,365,166 B2
(45) Date of Patent: Jul. 30, 2019

(54) ENVIRONMENTAL PARAMETER SENSOR

(71) Applicant: NXP B.V., Eindhoven (NL)

(72) Inventors: Kim Phan Le, Eindhoven (NL); Jozef Thomas Martinus van Beek, Rosmalen (NL); Niels Klemans, Eindhoven (NL)

(73) Assignee: NXP B.V., Eindhoven (NL)

( * ) Notice: Subject to any disclaimer, the term of this patent is extended or adjusted under 35 U.S.C. 154(b) by 149 days.

(21) Appl. No.: 15/196,962

(22) Filed: Jun. 29, 2016

(65) Prior Publication Data
US 2017/0003176 A1 Jan. 5, 2017

(30) Foreign Application Priority Data

Jul. 1, 2015 (EP) ..................................... 15174828

(51) Int. Cl.
*G01K 11/24* (2006.01)
*G01N 29/024* (2006.01)
(Continued)

(52) U.S. Cl.
CPC ........... *G01K 11/24* (2013.01); *G01N 29/024* (2013.01); *G01N 29/032* (2013.01); *G01N 29/14* (2013.01);
(Continued)

(58) Field of Classification Search
CPC ............ G01K 11/24; G01N 2291/011; G01N 2291/015; G01N 2291/0215;
(Continued)

(56) References Cited

U.S. PATENT DOCUMENTS

| 5,624,188 A | * | 4/1997 | West | G01K 11/24 374/119 |
| 2009/0215439 A1 | * | 8/2009 | Hamilton | H04M 1/605 455/418 |
| 2014/0064326 A1 | * | 3/2014 | Claussen | G01K 13/02 374/117 |

FOREIGN PATENT DOCUMENTS

| DE | 102011056533 A1 | 6/2013 |
| EP | 1591764 A1 | 11/2005 |

(Continued)

OTHER PUBLICATIONS

Prakash, K. S., O. P. Malik, and G. S. Hope. "Amplitude comparator based algorithm for directional comparison protection of transmission lines." IEEE transactions on power delivery 4.4 (1989): 2032-2041.*

(Continued)

*Primary Examiner* — Harshad R Patel

(57) ABSTRACT

An environmental parameter sensor for a mobile device is described comprising a first acoustic transducer; a second acoustic transducer arranged at a predetermined distance from the first acoustic transducer; a controller coupled to the first acoustic transducer and the second acoustic transducer; wherein the controller is configured to determine at least one of a time-of-flight value and an attenuation value of an acoustic signal between the first acoustic transducer and the second acoustic transducer and to determine at least one environmental parameter from the at least one of the time-of-flight value and the attenuation value The environmental parameter sensor may determine environmental parameters such as temperature, wind speed, and humidity from acoustic measurements.

15 Claims, 10 Drawing Sheets

(51) Int. Cl.
*G01N 29/032* (2006.01)
*G01N 29/14* (2006.01)
*G01N 29/46* (2006.01)
*G01S 15/88* (2006.01)
*G01N 29/38* (2006.01)
*G01N 29/44* (2006.01)
*G01N 29/48* (2006.01)

(52) U.S. Cl.
CPC ......... *G01N 29/38* (2013.01); *G01N 29/4436* (2013.01); *G01N 29/46* (2013.01); *G01N 29/48* (2013.01); *G01S 15/885* (2013.01); *G01N 2291/011* (2013.01); *G01N 2291/015* (2013.01); *G01N 2291/0215* (2013.01); *G01N 2291/02845* (2013.01); *G01N 2291/02881* (2013.01); *G01N 2291/048* (2013.01); *G01N 2291/102* (2013.01); *G01N 2291/103* (2013.01); *G01N 2291/105* (2013.01); *H04M 2250/12* (2013.01)

(58) Field of Classification Search
CPC .......... G01N 2291/02845; G01N 2291/02881; G01N 2291/048; G01N 2291/102; G01N 2291/103; G01N 2291/105; G01N 29/024; G01N 29/032; G01N 29/14; G01N 29/38; G01N 29/4436; G01N 29/46; G01N 29/48; G01S 15/885; H04M 2250/12

See application file for complete search history.

(56) References Cited

FOREIGN PATENT DOCUMENTS

| | | |
|---|---|---|
| JP | 3157902 B2 | 4/2001 |
| WO | WO-2013/179202 A3 | 12/2013 |

OTHER PUBLICATIONS

Extended European Search Report for Patent Appln. No. 15174828.2 (dated Dec. 23, 2015).

Wikipedia; "Mobile phone tracking"; retrieved from the internet https://en.wikipedia.org/wiki/Mobile_phone_tracking; 6 pages (Jun. 17, 2016.

* cited by examiner

ENVIRONMENTAL PARAMETER SENSOR

CROSS-REFERENCE TO RELATED APPLICATIONS

This application claims the priority under 35 U.S.C. § 119 of European patent application no. 15174828.2, filed Jul. 2, 2015 the contents of which are incorporated by reference herein.

FIELD

This disclosure relates to an environmental parameter sensor for a mobile device and a method of environmental parameter sensing for a mobile device

BACKGROUND

A mobile and smart device such as a smartphone is not simply a communication device but may act as a smart personal digital assistant (PDA). Recent generations of smartphones include a number of sensors such as accelerometers, gyroscopes, compass, pressure sensor, light sensor, temperature and humidity sensors. Some sensors are used to help improve user-input interfacing, some are used for navigation, and others are used to increase people's awareness about the surrounding environment such as temperature and humidity Ambient air temperature is one of the most interesting and basic environmental parameters that people want to know. Temperature perception of humans is usually not accurate. Temperature perception varies with seasons and is affected by a number of factors such as illness, wind, and dynamic changes in temperature. In many cases, smartphone users want to measure ambient temperature accurately, for example to check if an outdoor temperature is close to the freezing point to determine the danger of ice forming, whether a bedroom temperature is within the comfortable zone for an infant, or sharing locations on social media with local ambient temperature automatically attached.

SUMMARY

Various aspects are defined in the accompanying claims. In a first aspect there is defined an environmental parameter sensor for a mobile device comprising an acoustic output transducer; an acoustic input transducer arranged at a predetermined distance from the acoustic output transducer; and a controller coupled to the first acoustic transducer and the second acoustic transducer; wherein the controller is configured to determine at least one of a time-of-flight value and an attenuation value of an acoustic signal between the first acoustic transducer and the second acoustic transducer and to determine at least one environmental parameter from the at least one of the time-of-flight value and the attenuation value.

The environmental parameter sensor may sense environmental parameters such as ambient temperature, relative humidity and wind speed by a determination of the time-of-flight and/or relative amplitude or attenuation of an acoustic signal, that is to say an acoustic pressure wave or sound wave, at two points a predetermined distance apart. From this comparison, environmental parameters which affect the time of flight and attenuation of the acoustic signal may be determined. These parameters may include temperature, relative humidity, and wind speed and wind direction.

The first acoustic transducer and the second acoustic transducer may be for example a loudspeaker or a microphone.

Existing sensors incorporated into mobile devices such as mobile phones may include temperature sensors and relative humidity sensors. The temperature sensors may be affected by the temperature of the casing of the mobile phone for example, and self-heating of the phone from the electronic circuits. Complex algorithms may be used to at least partially compensate for these effects. Embodiments of the environmental parameter sensor used to measure temperature may respond to sudden changes in ambient temperature as the detected acoustic signal may be unaffected by the temperature of the mobile device. The environmental parameter sensor when included in to a mobile audio device may share some components used for other audio functions which require an acoustic transducer such as a speaker or a microphone.

Embodiments of the environmental parameter sensor may determine values of relative humidity and wind speed and compensate a measured temperature in order to improve the accuracy.

In embodiments of the environmental parameter sensor, the controller may be further configured to generate an acoustic signal waveform for transmission via the first acoustic transducer; detect the transmitted acoustic signal received via the second acoustic transducer; and to determine at least one of a time-of-flight value and an attenuation value of the acoustic signal from at least one of a time difference and an amplitude difference between the transmitted acoustic signal waveform and the received acoustic signal waveform.

In embodiments of the environmental parameter sensor, the controller may be configured to detect a first acoustic signal waveform via the first transducer, detect a second acoustic signal waveform via the second acoustic transducer and to determine the at least one of a time-of-flight value and an attenuation value of an acoustic signal from at least one of a time difference and an amplitude difference between the first acoustic signal waveform and the second acoustic signal waveform.

The acoustic signal which may have one or more frequency components which may be transmitted from a further acoustic transducer or from an external source. The first acoustic transducer and second acoustic transducer which may be for example microphones may detect the acoustic signal at different times.

Since the distance between the first and second acoustic input transducer may be predetermined, the environmental parameters may be calculated from a comparison of the respective signals detected via the first and second input transducers.

In embodiments of the environmental parameter sensor, the controller may be configured to determine the value of the speed of sound and to determine the at least one environmental parameter from the speed of sound and wherein the at least one environmental parameter comprises temperature.

Since the distance between the first acoustic transducer and the second acoustic transducer may be fixed and predetermined, a measurement of the time-of-flight of an acoustic signal between the transducers may be used to determine the speed of sound. The speed of sound varies with ambient temperature, so by determining a value of the speed of sound through the air, a value of ambient temperature may be determined. Since the speed of sound is also affected by wind speed and direction, a measured value of the speed of sound may be used to measure wind speed.

In embodiments of the environmental parameter sensor, the controller may comprise an acoustic signal waveform generator coupled to the first acoustic transducer, a signal detector coupled to the second acoustic transducer, and a parameter calculation module coupled to the signal detector and the acoustic signal waveform signal generator.

In embodiments of the environmental parameter sensor, the controller may comprise a signal detector coupled to the first acoustic transducer and the second acoustic transducer, and a parameter calculation module coupled to the signal detector.

Embodiments of the environmental parameter sensor including the parameter calculation module may comprise a delay calculation module operable to determine a time difference value between the acoustic signal waveform detected or emitted via the first acoustic transducer and the acoustic signal waveform detected via the second acoustic transducer.

By determining the time delay or time difference over a known distance between a reference signal which may correspond to an acoustic signal waveform detected or emitted via the first acoustic transducer, and a detected signal which may correspond to the acoustic signal waveform detected via the second acoustic transducer, the value of the speed of sound may be determined. A value of, for example, the ambient temperature may be calculated from the value of the speed of sound In embodiments of the environmental parameter sensor the delay calculation module may comprise a cross-correlator coupled to an interpolator.

By cross-correlating the acoustic signal waveform transmitted or detected by the first acoustic transducer with the acoustic signal waveform detected by the second acoustic transducer, a delay or time-of-flight of the acoustic signal between the first and second acoustic transducers may be determined. Embodiments using an interpolator may improve the accuracy of the estimation for low sample frequencies, for example equal or less than 96 KHz. For higher sample frequencies the interpolator may be omitted.

Alternatively or in addition use of a lock in method may be used for a sinusoidal reference signal which gives a value of phase delay. Provided the time period of the wave form satisfies the criteria:

$$Tf = 1/f \geq d/c1 - d/c2$$

in which Tf is the period of the waveform (in seconds), f is the frequency (in Hz) of the repeated waveform patterns (which is the frequency of the waveform if it is sinusoidal), d is the distance (in meters) between the sound emitter and the sound receiver, c1 and c2 (in m/s) are the speed of sound in air at the lowest and highest temperature in the range of interest, then the phase difference between the reference signal and detected signal may also represent the time delay or time of flight for the acoustic signal to be transmitted over the distance d.

Alternatively or in addition a fast Fourier transform (FFT) module may be used to determine the phase difference and consequently the time delay.

In an embodiment of the environmental parameter sensor, the controller may further comprise an amplitude comparator, wherein the acoustic signal waveform comprises a first reference frequency and a second reference frequency and the controller is operable to determine the at least one environmental parameter from the attenuation of the acoustic signal and wherein the at least one environmental parameter comprises the relative humidity.

Since the amplitude of the sound wave may be attenuated dependent on relative humidity, measuring the attenuation of the reference frequency over a known distance may be used to determine a value for relative humidity. Higher frequencies tend to attenuate more rapidly than lower frequencies. By having an acoustic signal having a first reference or evaluation frequency, for example 20 KHz and a second higher reference frequency, for example 80 KHz, two values of attenuation may be determined. The attenuation value of the 20 KHz waveform may be used as a baseline to compensate for differences in mobile devices in which the environmental parameter sensor may be incorporated which may result in a more accurate reading than using a single evaluation frequency. The determined value of relative humidity may be used to compensate the temperature. Alternatively a dedicated relative humidity sensor may be used.

In embodiments of the environmental parameter sensor, the controller may be configured to determine a further time of flight value of the acoustic signal between the first acoustic transducer and the second acoustic transducer and wherein the at least one environmental parameter comprises a wind speed value the controller may be configured to determine a wind speed value from a difference between the time of flight value and the further time of flight value.

In embodiments of the environmental parameter sensor the controller may be configured to determine the time of flight value is determined in a first orientation of the environmental parameter sensor and the further time of flight value in a further orientation of the environmental parameter sensor.

By taking two measurements in different orientations, typically a second measurement in a direction within 10 degrees of 180 degrees compared to the first measurement, a value for the wind speed component may be determined.

In embodiments of the environmental parameter sensor the controller may determine a compensated temperature in dependence of the determined wind speed component.

In embodiments, the environmental parameter sensor may be configured as at least one of a temperature sensor, a wind vector sensor, and a relative humidity sensor.

Embodiments of the environmental parameter sensor may be included in mobile devices such as smart-phone, tablet, and wearable electronic device, for example a smart watch, handheld navigation device, walkie-talkie, or headsets such as a Bluetooth headset or active noise cancelling headset. If these mobile devices include other audio functions, the first acoustic transducer, which may be for example a loudspeaker, and the second acoustic transducer, which may be for example a microphone, may be shared with other audio functions so providing an environmental parameter sensor with a reduced number of components.

In a second aspect there is described a method of environmental sensing for a mobile device comprising: determining at least one of a relative amplitude and a time-of-flight of an acoustic signal between a first acoustic transducer and a second acoustic transducer; determining a value of at least one environmental parameter from at least one of the relative amplitude and the time-of-flight.

Embodiments of the environmental sensing method use an acoustic signal to determine one or more environmental parameter values such as temperature and relative humidity of ambient air using a mobile device.

Embodiments may also be incorporated into a motor vehicle including an audio system which may include for example a loudspeaker and a hands free microphone. When implemented in a motor vehicle audio system, the method may be used for example to measure the air temperature inside the cabin of the motor vehicle.

In embodiments, determining the at least one of a relative amplitude and a time-of-flight of the acoustic signal may comprise generating an acoustic signal; emitting the acoustic signal from the first acoustic transducer; detecting the emitted acoustic signal via the second acoustic transducer and determining at least one of a time difference and an amplitude difference between the generated acoustic signal and the detected acoustic signal.

In embodiments determining the time-of-flight of the acoustic signal may comprise generating an acoustic signal; emitting the acoustic signal from a further transducer, detecting the emitted acoustic signal via the first acoustic transducer; detecting the emitted acoustic signal via the second acoustic transducer and determining at least one of a time difference and an amplitude difference between the generated acoustic signal and the detected acoustic signal.

In a third aspect there is described a computer program product comprising instructions which, when being executed by a processing unit, cause said processing unit to perform a method of environmental sensing for a mobile device comprising: determining at least one of a relative amplitude and a time-of-flight of an acoustic signal between a first acoustic transducer and a second acoustic transducer; determining a value of at least one environmental parameter from at least one of the relative amplitude and the time-of-flight.

BRIEF DESCRIPTION OF DRAWINGS

In the figures and description like reference numerals refer to like features. Embodiments of the invention are now described in detail, by way of example only, illustrated by the accompanying drawings in which.

DESCRIPTION

Figure 1:
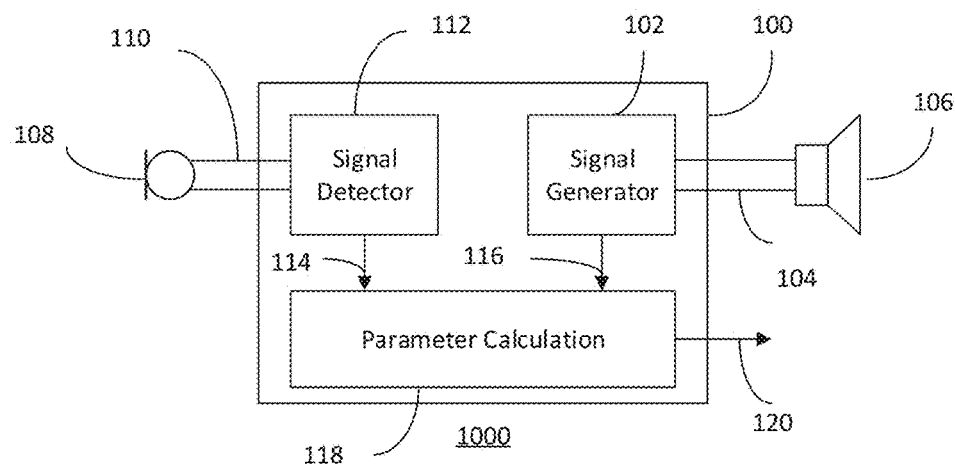
FIG. 1 shows an environmental parameter sensor according to an embodiment.

FIG. 1 shows an environmental parameter sensor 1000. A signal generator 102 may generate an acoustic signal waveform. An output of the signal generator 102 may be connected to a loudspeaker 106. A reference signal output 116 of signal generator 102 may be connected to a parameter calculation module 118. A signal detector 112 may have an input 110 connected to a microphone 108. The signal detector 112 may have an output 114 connected to the parameter calculation module 118. The parameter calculation module may have an environmental parameter output 120. The signal generator 102, the signal detector 112 and the parameter calculation module 118 may be included in a controller or signal processing unit 100.

In operation the signal generator 102 may generate an acoustic signal waveform. The generated waveform may have a frequency in the audible, ultrasound or infrasound frequency range. The generated waveform may be a continuous waveform such as, in the audible range, a piece of music or a series of tones. The generated waveform may be a pulse, chirp, pseudo-random noise, or one or more sinusoidal waves. The generated waveform may be emitted by the loudspeaker 106 as an acoustic wave or signal such as a sound wave or ultrasound wave. The acoustic wave may be detected by the signal detector 112 via the connected microphone 108. The parameter calculation module 118 may receive a reference signal from the signal generator 102. The reference signal may be the generated waveform or a delayed version of the generated waveform which corresponds to the acoustic signal emitted via the loudspeaker 106. The parameter calculation module 118 may receive a detected acoustic signal waveform from the signal detector 112 corresponding to the signal received via the microphone 108. The parameter calculation module 118 may determine a value of one or more environmental parameters such as ambient air temperature, relative humidity and wind speed from the signal properties of the detected acoustic signal, such as relative amplitude and/or phase or time delay, with respect to the reference signal.

Since the distance between the loudspeaker 106 and the microphone 108 is known, by determining the phase lag or time delay between the detected signal and the reference signal, a measurement of the value of the speed of sound through the air may be determined, which in turn may be used to determine one or more environmental parameter values.

The speed of sound in an ideal gas can be expressed by the following equation:

$$c_{air} = \sqrt{\gamma k T/m} \, (m/s) \qquad (1)$$

in which γ is the adiabatic index, k is the Boltzmann constant, T is the absolute temperature in Kelvin, and m is the mass of a single gas molecule in kilograms. For dry air, the formula can be simplified to:

$$c_{dry-air} = 20.05\sqrt{T} \text{ (m/s)} \quad (2)$$

Within a temperature range of −20 degrees C. to +40 degrees, the relationship is very close to a linear function with the speed of sound varying between 320 m/s to 355 m/s. The slope of the change is about 0.18% per degree.

Hence, for dry air, a measurement of speed of sound may be used to determine a value of air temperature. The speed of sound ($c_{air}$) can be calculated from the distance that an acoustic wave such as a sound wave travels (d) and the time it takes to do so (t): $c_{air}=d/t$. In a measurement, if distance d is known, $c_{air}$ can be derived if the time delay between sending and receiving a sound wave can be measured. Hence in environmental parameter sensor 1000, by sending a sound wave from the loudspeaker 106 to a microphone 108 having a fixed mutual distance, the parameter calculation module 118 may determine a value of the air temperature by calculating the phase lag (or phase delay, phase shift) between the emitted and received signal which may correspond to the time delay between sending and receiving a sound wave and so gives a measure of the time of flight of the sound wave.

The measured value of the speed of sound may also be affected by wind speed. When the wind component $v_{wind\_comp}$ is in the same direction of sound, the speed of sound increases by $v_{wind\_comp}$, that is: $c_{for}=c_0+v_{wind\_comp}$, in which $c_0$ is the speed of sound in calm air. When the wind component $v_{wind\_comp}$ is in the opposite direction of sound, the speed of sound decreases by $-v_{wind\_comp}$, that is: $c_{against}=c_0-v_{wind\_comp}$.

The environmental parameter sensor 1000 may make at least two measurements in substantially opposite directions, which results in two speeds of sound $c_{for}$ and $c_{against}$. The two measurements in opposite directions may be made by orienting the environmental parameter sensor 1000 at a first direction, and then rotating the environmental device approximately 180°. The speed of sound in calm air may be calculated by averaging these two speeds: $c_0=(c_{for}+c_{against})/2$. From the value of $c_0$, a value of ambient air temperature may be calculated by parameter calculation module 118 compensating for the effect of wind speed. The parameter calculation module 118 may determine a value of wind speed by determining $(c_{for}-c_{against})/2$. It will be appreciated that the accuracy of the wind speed measurement may be improved by aligning the environmental parameter sensor 1000 such that the axis between the microphone 108 and the loudspeaker 106 is aligned with the direction of the wind during the measurement.

The environmental parameter sensor 1000 may also determine a measure of relative humidity (RH). Absorption of sound in air is a function of RH and frequency. The effect is large especially when sound travels over a long distance. Over distances in the range of about 10-15 cm, the effect is rather small. Nevertheless, this effect may still be used to estimate RH. Sound waves at two different frequencies, such as at 18 kHz and 80 kHz, may be generated by the signal generator 102 and emitted from the speaker 106. The respective received sound levels may be compared in parameter calculation module 118, and a value of RH determined from the received sound levels. The measurement at a lower frequency may be used as a reference to improve accuracy, although a single frequency may be used. Since the speed of sound is also affected by relative humidity, the determined relative humidity value may also be used to adjust a determined value of the speed of sound from which an ambient temperature reading may be determined.

The environmental sensor 1000 may be implemented in hardware or a combination of hardware and software. For example the parameter calculation module 118, the signal generator 102 and the signal detector 112 may be implemented as hardware modules or as software running on a digital signal processor (DSP). In the case of software implementation on a DSP the signal detector 112 may be interfaced to a microphone using an analog to digital converter (not shown) and the signal generator 102 may be interfaced to the loudspeaker 108 using a digital to analog converter (not shown).

The environmental sensor 1000 may be incorporated into a mobile device such as a mobile phone. In this case the speaker 106 may also be used as the receiver speaker, and the microphone 108 may also be used as the voice microphone during a phone call. The environmental sensor 1000 may therefore be implemented at lower cost by sharing components.

Figure 2:
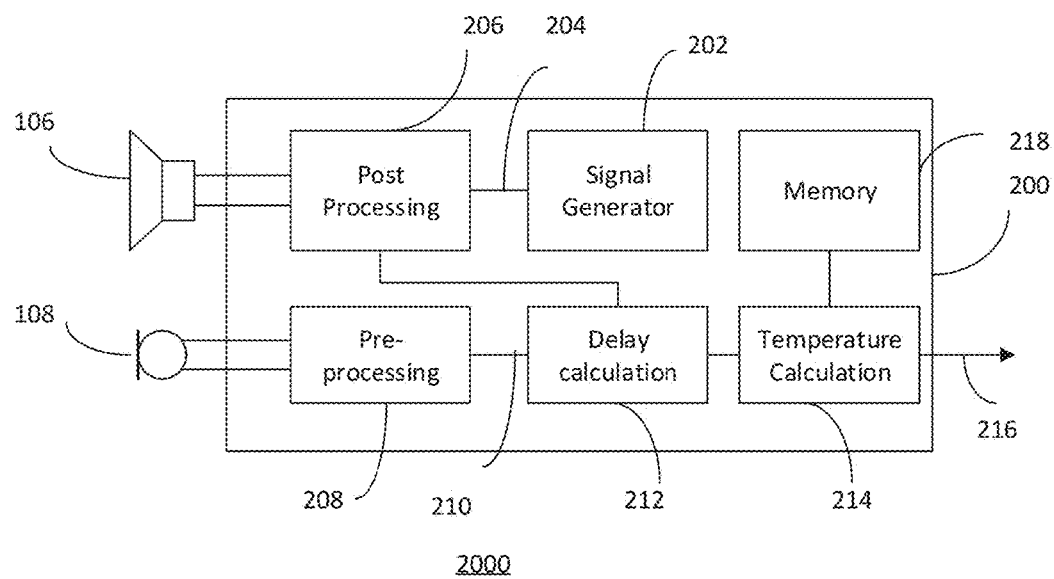
FIG. 2 illustrates an environmental parameter sensor for temperature sensing according to an embodiment.

FIG. 2 shows an environmental parameter sensor 2000 which may be used to determine an ambient air temperature. A signal waveform generator 202 may be connected to post processing module 206 an output of the post processing module 206 may be connected to a loudspeaker 106. A reference signal output 204 from the post processor 206 may be connected to a delay calculation module 212. A pre-processing module 208 may have an input connected to a microphone 108. An output 210 of the pre-processing module 208 may be connected to an input of the delay calculation module 212. An output of the delay calculation module 212 may be connected to temperature calculation module 214. The temperature calculation module 214 may be connected to a memory 218. Temperature calculation module may output a value representative of an ambient temperature on output 216. The signal waveform generator 202, the post processing module 206, the pre-processing module 208, the delay calculation module 212, the temperature calculation module 214 and the memory 218 may be included in a controller or a signal processing unit 200. The delay calculation module 212, the temperature calculation module 214 and the memory 218 may be included in a parameter calculation module.

The environmental sensor 2000 may be implemented in hardware or a combination of hardware and software. For example the signal generator 202, the delay calculation module 212, and the temperature calculation module 214 may be implemented as hardware modules or as software running on a digital signal processor (DSP) or a microprocessor.

In operation, the signal waveform generator 202 may generate an acoustic signal waveform. The frequency range of the generated waveform may be infrasonic, audible or ultrasonic. The waveform may be a periodic waveform such as a sinusoid, square wave, or saw tooth, or non-periodic waveform such as a chirp, or pulses or pseudo random noise, or any auditory tone or piece of music or speech. The frequency range of the acoustic signal can be any range, such infrasonic, audible, or ultrasonic. If the sound wave is a periodic waveform, its period may be equal or longer than the total difference in the time of flight over the whole temperature range of interest. If a phase comparison technique is used to determine a time delay this may avoid ambiguity in defining temperature from phase lag information. The signal waveform frequency may satisfy the following criteria.

$$Tf = 1/f \geq d/c1 - d/c2 \quad (3)$$

in which Tf is the period of the waveform (in seconds), f is the frequency (in Hz) of the repeated waveform patterns (which is the frequency of the waveform if it is sinusoidal), d is the distance (in m) between the sound emitter and the sound receiver, c1 and c2 (in m/s) are the speed of sound in air at the lowest and highest temperature in the range of interest, respectively. For instance, for consumer electronics, the temperature of interest is from −20° C. to +40° C. Over this temperature range, the speed of sound changes from 320 m/s (c1) to 355 m/s (c2). For a distance between a speaker and a microphone of 12 cm, according to equation 3, Tf should be equal or larger than 37 µs or equivalent to a pattern frequency of equal or lower than 27 kHz. In this example, if the waveform is a sinusoid and the frequency is less than or equal to lower than 27 kHz, a phase lag comparison technique may be used to determine the time delay.

The signal waveform generator 202 may output an acoustic signal waveform to the post processor 206 which may consist of a measurement circuit for measuring the voltage and/or current of the output signal. The speaker 106 may transmit the acoustic signal waveform. The post processor 206 may also output a reference signal waveform to the delay calculation module 212. The sound wave or acoustic signal emitted by the speaker 106 may be detected by the microphone 108. The output signal from the microphone may be input into the pre-processor 208 of the controller 200. The pre-processor 208 may include an analog to digital convertor. The pre-processor 208 may include one or more of an audio preamplifier, a filter, a decimator, and an interpolator. The delay calculation module 212 may receive a reference signal waveform on input 204 and a detected acoustic signal waveform on input 210. The delay calculation module 212 may compare phases of the two signal waveforms and output a phase difference value θ. The phase difference value θ, may correspond to the delay between the transmitting the acoustic signal via the speaker 106 and detecting the acoustic signal via the microphone 108. Alternatively the delay between the two signal waveforms may be determined directly by, for example, cross-correlation. The temperature calculation module 214 may determine an ambient temperature from the calculated delay and various calibration parameters such as the distance between the speaker 106 and the microphone 108 which may be stored in the memory 218. As the determined delay may correspond to the elapsed time or time of flight t it takes for the acoustic signal to travel from the speaker 106 to the microphone 108, knowing the fixed distance in between the speaker and the microphone, the speed of sound in air can be calculated. Ambient air temperature can be subsequently calculated from the speed of sound using the relationship in Equation (2), or even more precisely using a relationship that has been derived from calibration measurements performed particularly for the mobile device during its development in the factory. The air temperature information may subsequently be used further by a circuit or software (not shown) in a mobile device including the environmental parameter sensor 2000, to be shown on the display of the mobile device.

Some smart phones use dedicated temperature sensors integrated circuits to measure air temperature. The integrated circuit is typically mounted on a printed circuit board, and together with hundreds of other components, housed inside the phone's case. The whole system may have a large equalization time of about 40 minutes to an hour or more which makes the response time to changes in ambient air, occurring for example when a user goes from indoors to outside. The self-heating of the phone may also affect the accuracy of the temperature reading. For instance many dissipating components like the central processor unit (CPU), and battery may heat up the phone by a few degrees to a few tens of degrees compared to ambient temperature. The heating effect may depend on the operation mode of the phone. To compensate for this, a compensation algorithm may be used to correct for the slow behaviour of the sensor signal and remove the influence of the self-heating based on various readings in the phone such as battery temperature, CPU loading, CPU temperature. However, this algorithm may be complex and may only work under some restricted circumstances and well defined use cases.

Temperature may be measured using long wave infrared (LWIR) detector. An LWIR detector (or camera) in a phone may sense the temperature of the surrounding objects (such as a wall) to deduce ambient air temperature. However, this technique requires an LWIR detector in phones which is usually very expensive. Furthermore LWIR detection actually measures the temperature of a solid object which may be different to the ambient air temperature. In addition the accuracy of the temperature measurement may depend on the emissivity of the objects which may vary largely depending on materials.

Figure 3:
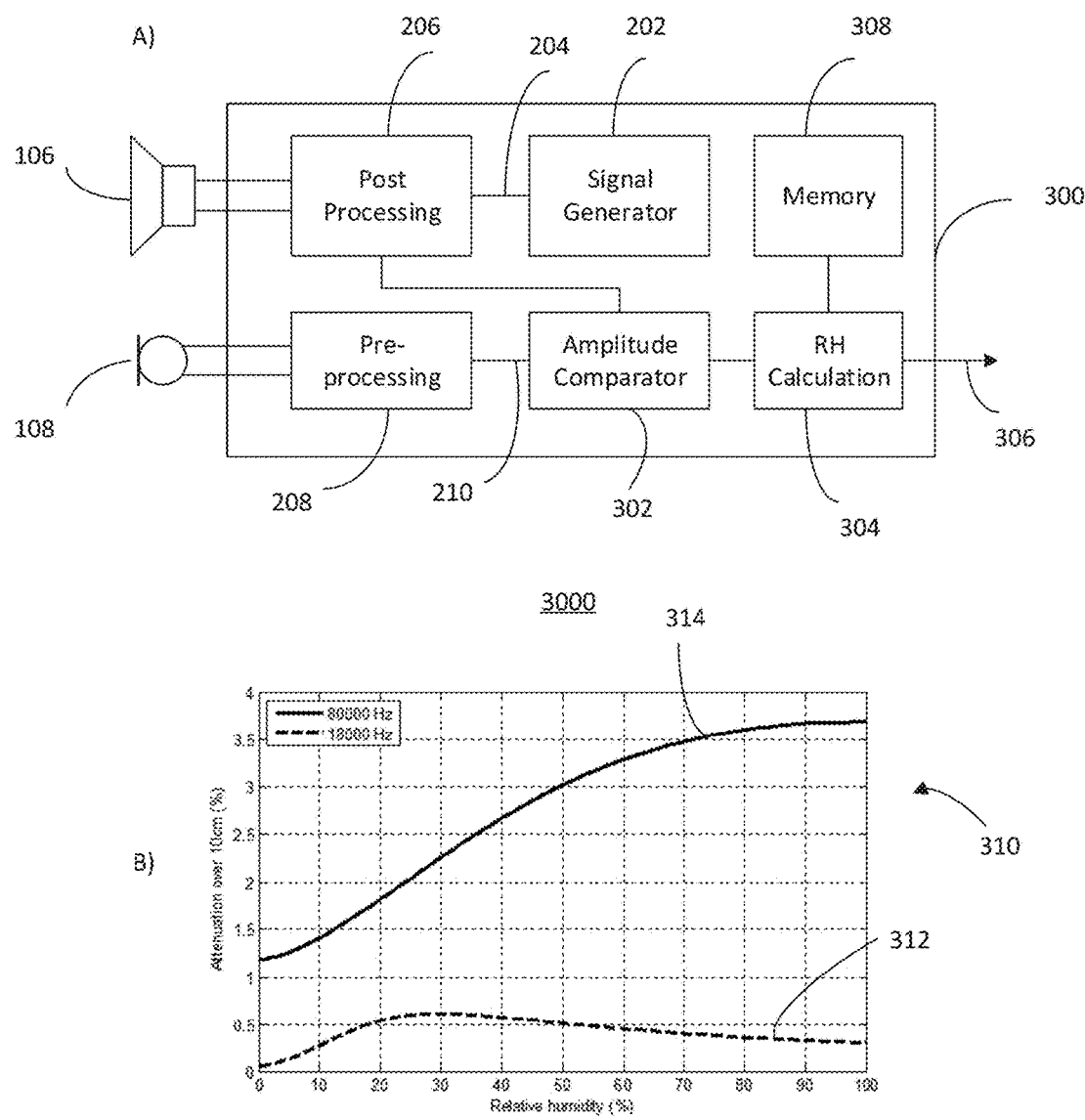
FIG. 3 shows a) an environmental parameter sensor for relative humidity sensing according to an embodiment and b) a graph illustrating the attenuation of relative humidity over distance for two different frequencies

FIG. 3A shows an environmental parameter sensor 3000 which may be used to determine a value of relative humidity. A signal waveform generator 202 may be connected to post processing module 206. An output of the post processing module 206 may be connected to a loudspeaker 106. A reference signal output 204 from the post processor 206 may be connected to an amplitude comparator 302. A pre-processing module 208 may have an input connected to a microphone 108. An output 210 of the pre-processing module 208 may be connected to an input of the amplitude comparator 302. An output of the amplitude comparator 302 may be connected to relative humidity calculation module 304. The relative humidity calculation module 304 may be connected to a memory 308. The relative humidity calculation module may output a value representative of the relative humidity on environmental parameter sensor output 306. The signal waveform generator 202, the post processing module 206, the pre-processing module 208, the amplitude comparator 302, the RH calculation module 304 and the memory 304 may be included in a controller 300 or a signal processing unit. The amplitude comparator 302, the RH calculation module 304 and the memory 304 may be included in a parameter calculation module.

The signal waveform generator 202 may output an acoustic signal waveform to the post processor 206. The acoustic signal waveform may include a sinusoid having a first frequency, for example 20 KHz and a sinusoid having a second frequency for example 80 KHz. The generated signal may include the two sinusoidal waveforms simultaneously or sequentially. The post processor 206 may consist of a measurement circuit for measuring the voltage and/or current of the output signal. The speaker 106 may transmit the acoustic signal waveform. The post processor 206 may also output a reference signal corresponding to the generated signal on post processor output 204. The sound wave or acoustic wave emitted by the speaker 106 may be detected by the microphone 108. The output signal from the microphone may be input into the pre-processor 208 of the controller 300. The pre-processor 208 may include an analog to digital convertor. The pre-processor 208 may include one or more of an audio preamplifier, a filter, a decimator, and an interpolator. The pre-processor 208 may output the detected signal on output 210. The amplitude comparator 302 may receive a reference signal and a detected signal. The amplitude comparator 302 may determine a relative amplitude difference between the reference signal and the detected signal and output the detected amplitude difference to the RH calculation module 304. The RH calculation module may determine a value of relative humidity from a predetermined set of parameters stored in the memory 308.

FIG. 3B shows a graph 310 of an example variation of relative humidity as a percentage on the X-axis versus the percentage attenuation over 10 centimeters on the Y axis. Curve 312 shows the variation for a frequency of 18 KHz from approximately 0.1 percent at 0 percentage relative humidity increasing to a peak value of approximately 0.6 percent at 25 percent relative humidity and then declining to a value of 0.4 percent attenuation at 100 percent relative humidity. Curve 314 show the variation for a frequency 80 KHz. Curve 314 indicates a percentage attenuation of approximately 1.2 percent at 0 percent relative humidity which increases to a value of approximately 3.6 percent at 100 percent relative humidity. It will be appreciated that the values on the two curves may be include for example in a lookup table in memory 318 which may then be used by the RH calculation module 304 to determine a value of relative humidity from the relative amplitude difference between the generated acoustic reference signal waveform and the detected signal waveform. It will be appreciated that the attenuation of other frequencies with respect to relative humidity may also be characterized over the same distance and other distances.

Figure 4:
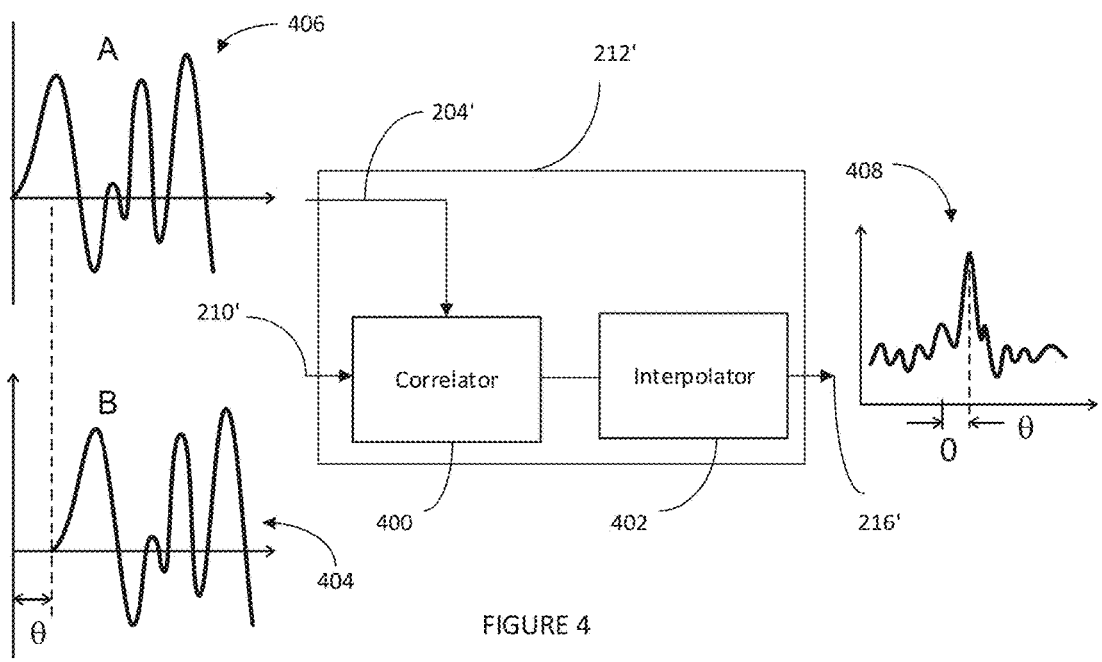
FIG. 4 shows an example delay calculation module which may be used in embodiments of the environmental parameter sensor.

FIG. 4 illustrates an example delay calculation module 212' which may for example be included in the environmental parameter sensor 2000. Delay calculation module 212' may include a cross-correlator 400 which may be connected to an interpolator 402. A reference signal waveform 406 may be generated and input to the correlator 400 on input 204'. A detected signal waveform 404 may be received on the input 210' of the correlator 400. The interpolator 402 may generate an interpolated output from the cross-correlated output for example using a quadratic fit or Gaussian sinusoidal fit algorithm.

The delay calculation module 212' may cross-correlate the detected signal with the reference signal. It will be appreciated that a time delay θ may be determined from the horizontal distance between the mid-point in the x-axis value corresponding to the mid-point of a cross-correlated output curve 408 and the x-axis value corresponding to the peak of the cross correlated output curve 408. The delay may be determined between signals where the delay between the reference signal and the detected signal is within one cycle or greater than one cycle.

In practice, the cross-correlation curve may be discretized in both amplitude and time axes. The amplitude resolution may be defined by the bit depth which may be for example 16 bit or 24 bit. The time resolution is defined by Ts=1/Fs, where Ts is the time interval between consecutive sampling points, and Fs is the sampling rate of the audio signal, usually 44.1 kHz for audio CD quality, 48 kHz DVD audio quality, or 96 kHz Blu-ray and professional audio equipment quality. In many mobile devices Fs is 44.1 kHz or 48 kHz, and higher rates are not necessary. When the delay, thus consequently temperature information, is determined by finding the cross-correlation peak, the time resolution of the signal will set the resolution of the obtained temperature information.

Figure 5:
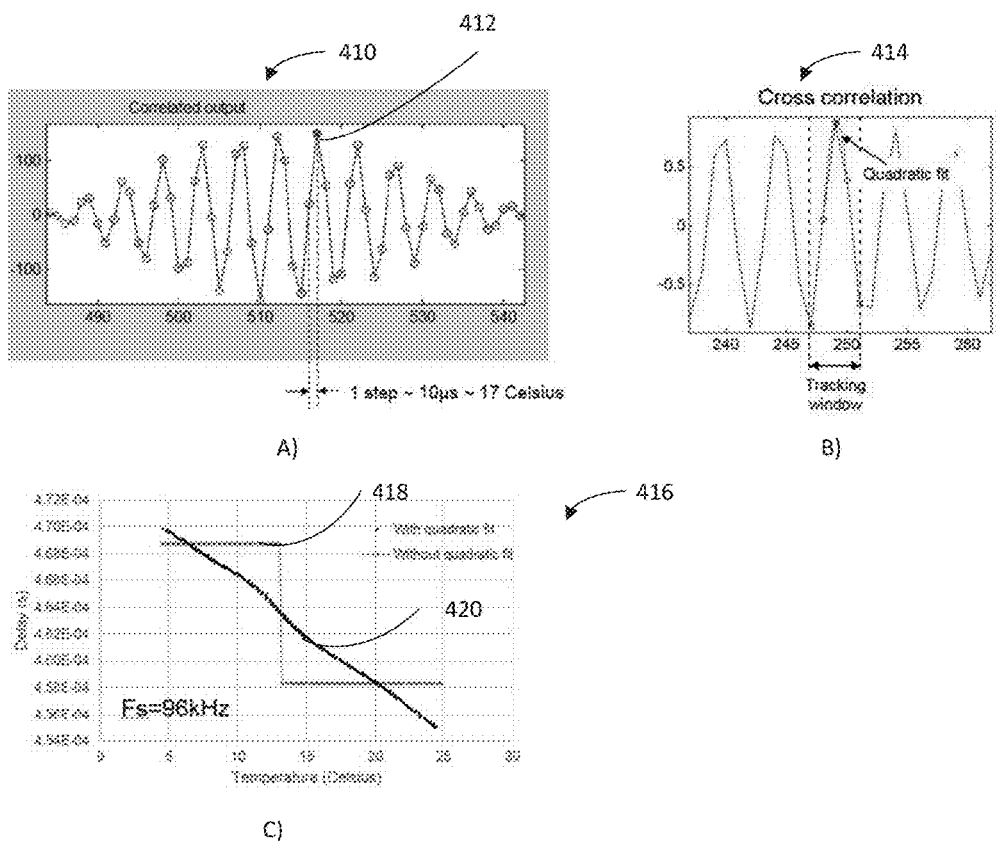
FIG. 5 shows a) a graph of a correlated output of the delay calculation module of FIG. 4; b) a graph of an interpolated cross-correlation output of the delay calculation module of FIG. 4; and c) a graph of a comparison of a cross-correlation result with and without interpolation.

FIG. 5A shows a zoomed in cross-correlation curve 410 around the peak 412. The sampling rate of the detected signal in this example is 96 kHz, and the signal band is around 20 kHz (ultrasound). The round symbols indicate actual sampling points. The peak 412 is the point based on which temperature can be determined. When ambient temperature changes, the horizontal location of the peak changes. However, due to the discretization of the curve, the peak location can only jump minimum one step at a time, which is equivalent to approximately 10 μs or approximately 17° C. That means, at a sampling frequency of 96 kHz, the best temperature resolution can only be 17° C. In order to resolve ±1° C., the sampling rate must be ≥806 kHz, which is not possible in all audio electronics.

The interpolator 400 may improve the resolution of temperature by a trade-off between amplitude resolution and time resolution. FIG. 5B shows a first example where a narrow searching window is defined around the expected peak, and a quadratic fit is performed within this window. From the fit parameters, a precise peak location, which is the peak of the fit parabola, may be calculated with extremely good resolution. FIG. 5C shows in graph 416 an example measurement in which ambient temperature was varied from 5° C. to 25° C., while the acoustic signal was received and cross correlation with the transmitted acoustic signal was calculated for a sample frequency of 96 KHz. The delay which is corresponding to the calculated temperature vs. real ambient temperature curves obtained by simple peak finding 418 and by quadratic fit 420 are illustrated. Without using the quadratic fit interpolation, the delay curve 418 has large steps of approximately 17° C., while using the quadratic fit results in a curve 420 with very fine steps, corresponding to a resolution of less than 0.2° C. In alternative implementations interpolator 400 may use a Gaussian sinusoidal fit which may fit a much larger number of data points around the expected peak. A Gaussian sinusoidal fit may allow a high temperature resolution of less than 0.2° C. to be obtained with a lower sampling rate of 48 kHz. In examples of the delay calculation module where higher sample rates are used, the interpolator may be omitted.

The reference acoustic signal may be a signal of short duration, which may be for example below 10 milliseconds. In this case, any signal component detected due to a reflection from a nearby object may be discriminated by time windowing the cross correlation, since the reflected signal may arrive later than the time window that is used to receive the direct signal from the acoustic transducer or loudspeaker. Alternatively the generated reference signal may be a large bandwidth signal for example having a bandwidth greater than 10 KHz. Using a large bandwidth signal may result in a narrower cross-correlation peak which may be more easily discriminated from peaks caused by reflected signals. In other examples, an adaptive cancellation technique may be used since reflections may be detected from the reflection peaks in the cross-correlation curve. Knowing the time delay of the reflection paths in any signal processing iteration, the reflection may be effectively cancelled in the next iteration in the time domain signal by subtracting the delayed signal from the received signal. Further, since the time delay of reflected paths are also determined, the sensor may also be used as a proximity sensor to detect, for example, when the reflections are caused by a user's hand being close to the environmental parameter sensor.

Figure 6:
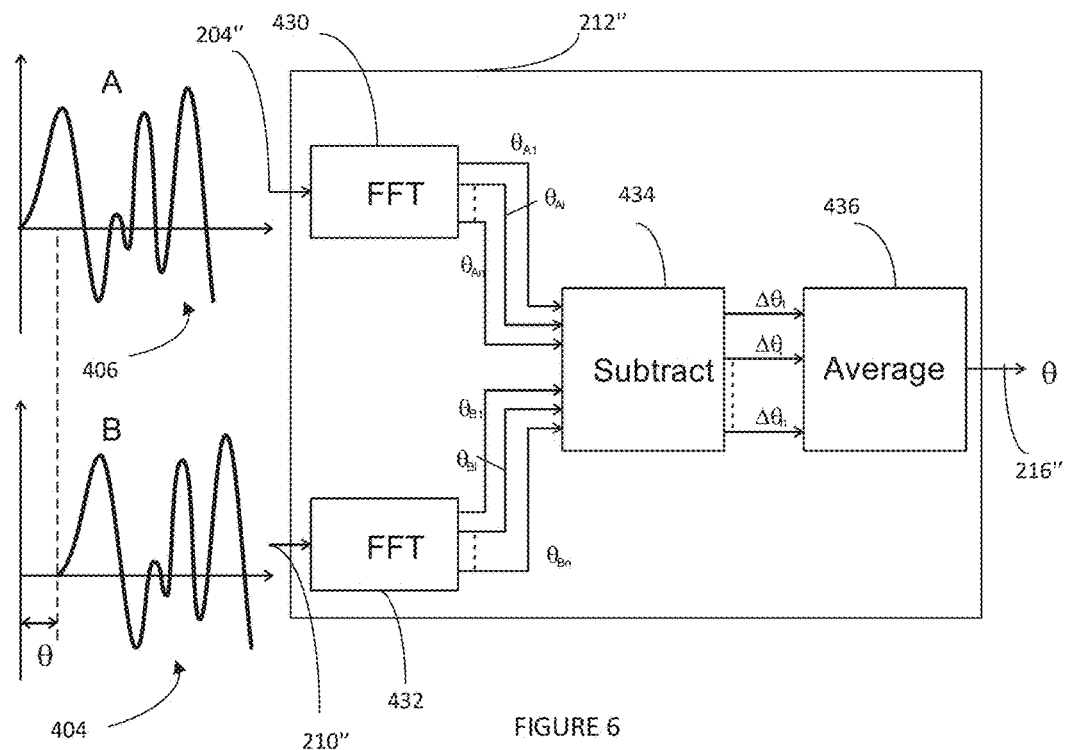
FIG. 6 shows an example delay calculation module which may be used in some embodiments of the environmental parameter sensor.

FIG. 6 shows a delay calculation module 212" having a first fast Fourier transform module 430 and a second fast Fourier transform module 432. First FFT module 430 may have an input 204" which in operation receives a reference acoustic signal waveform 406. Second FFT module 432 may have an input 210" which in operation receives a detected signal waveform 404. The output of the first FFT module may be connected to a subtractor 434. The output of the second FFT module may be connected to the subtractor 434. The outputs of the subtractor 434 may be connected to an averaging module 436. In operation, the first FFT module 430 may output a number of phases of different frequency components of the reference signal 406 denoted $\theta_{A1}$ to $\theta_{AN}$. The second FFT module 432 may output a number of phases of different frequency components of the detector signal 404 denoted $\theta_{B1}$ to $\theta_{BN}$. Since air may be considered a non-dispersive medium, the sound speed is independent of the sound frequency. Consequently the phase shift of all the FFT components may be the same. The subtractor module 434 may subtract a phase of a particular frequency component output from the first FFT module 430, for example $\theta_{A1}$ from a phase of the same frequency component output from the second FFT module for example en to give a value of the phase shift $\theta$. The averager 436 may average multiple phase differences to improve the accuracy of the value of the phase shift $\theta$ output at the averager output 216". The delay calculation module 212" may determine a phase shift from a single frequency component for example the fundamental harmonic or an averaged value of frequency components. Where the time delay is less than the duration of one cycle of the reference frequency, the phase shift or phase lag may correspond to the time delay between the generated signal being transmitted from a speaker or other acoustic transducer and being detected by a microphone or other acoustic transducer.

Figure 7:
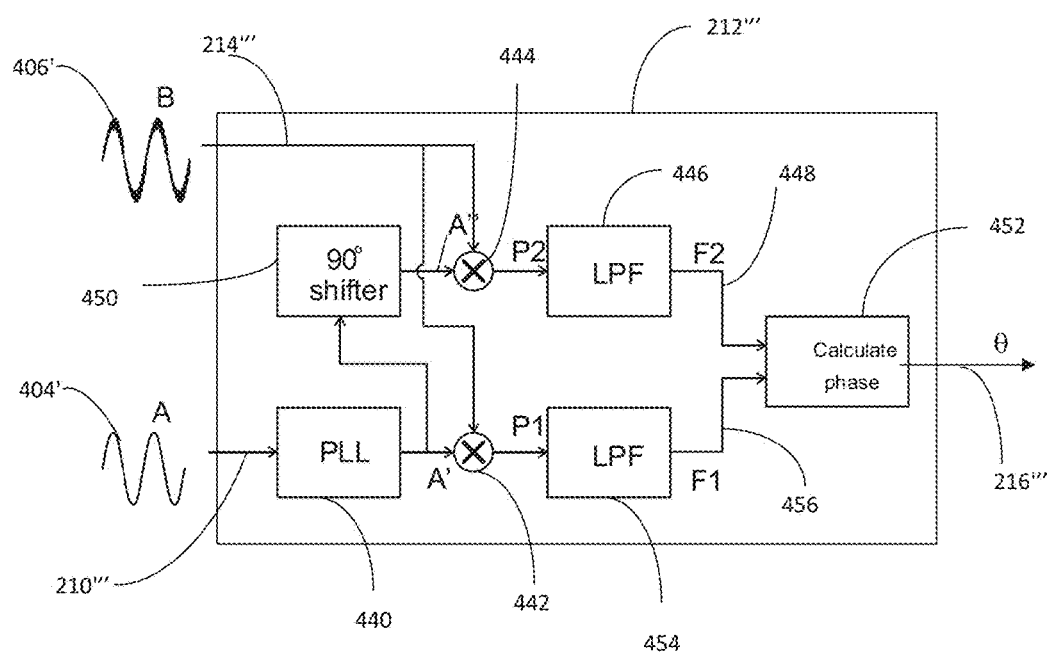
FIG. 7 shows an example delay calculation module which may be used in some embodiments of the environmental parameter sensor.

FIG. 7 shows a delay calculation module 212''' including a Phase Locked Loop (PLL) 440 having a first phase comparator input 210'''. An output of the PLL 440 may be connected to a multiplier or mixer 442. An output of a PLL 440 may be connected to a 90° shifter 450 and an output of 90° phase shifter 450 may be connected to an input of a second mixer multiplier 444. A phase comparator input 214''' may be connected to the first mixer 442 and the second mixer 444. An output of the first mixer 442 may be connected to a first low pass filter 454. An output 456 of the first low pass filter 454 may be connected to an input of a phase calculation module 452. An output of the second mixer 444 may be connected to a second low pass filter 446. An output 456 of the second low pass filter 446 may be connected to an input of a phase calculation module 452. The phase calculation module 452 may have a phase calculation output 216".

In operation of delay calculation module 212''', a reference acoustic sinusoidal waveform 404' denoted A, as may be input into a phase locked loop (PLL) 440. The PLL 440 may produce a clean sinusoidal waveform denoted A' with a fixed amplitude and phase following exactly the original waveform A. If waveform A is also sinusoidal and clean, that is to say does not include any significant noise component, then the PLL 440 can be omitted. At the output of the PLL 440, a clean, and so-called reference signal is produced, which can be expressed as: $A'=V_{ref}\sin\omega t$, in which $\omega$ is the frequency of the waveform. The received waveform 406' denoted as B has the same frequency but with a different phase and can be expressed as: $B=V_B \sin(\omega t+\theta)$.

Waveform A' and B are multiplied in the first multiplier 442 which results in a product that has the following form:

$$P1=\tfrac{1}{2}V_B V_{ref}\cos\theta - \tfrac{1}{2}V_B V_{ref}\cos(2\omega t+\theta) \tag{4}$$

Signal P1 is then passed through the first low-pass filter (LPF) 454 which filters out the $2\omega$ component and as a result, signal F1 at the output of the LPF 454 is $$F1=\tfrac{1}{2}V_B V_{ref}\cos\theta \tag{5}$$

In a second signal path, waveform A' is 90 degree phase-shifted by phase shifter 450 to produce a phase shifted waveform denoted A". Next, A" is multiplied with B in a second multiplier and results in product P2:

$$P2=-\tfrac{1}{2}V_B V_{ref}\sin\theta - \tfrac{1}{2}V_B V_{ref}\cos(2\omega t+\theta+90) \tag{6}$$

Again, after a second LPF block 446 signal F2 will become:

$$F2=-\tfrac{1}{2}V_B V_{ref}\sin\theta \tag{7}$$

The calculate phase module 452 may determine the phase delay angle $\theta$ from equations (5) and (7) and output the value of phase delay angle $\theta$ on output 216".

The delay calculation module 212''' makes use of the lock-in principle which may improve the noise immunity from noise added to waveform B. The delay calculation module 212''' may be selective to a very narrow band round the signal of interest, therefore noise may be effectively suppressed.

Figure 8:
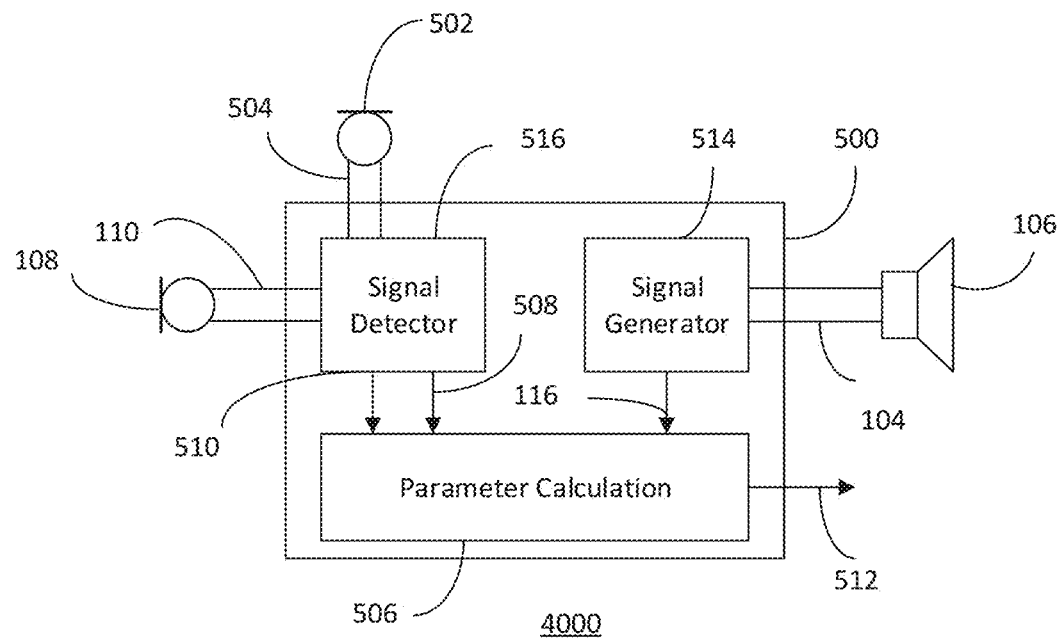
FIG. 8 illustrates an environmental parameter sensor according to an embodiment.

FIG. 8 shows an environmental parameter sensor 4000. A signal generator 514 may generate an acoustic signal waveform. An output 104 of the signal generator 514 may be connected to a loudspeaker 106. A signal detector 516 may have an input 110 connected to a microphone 108. The signal detector 514 may have a second input 504 connected to a second microphone 502. The signal detector 516 may have a first detector output 508 connected to the parameter calculation module 506. The signal detector 516 may have a second detector output 510 connected to the parameter calculation module 506. The parameter calculation module 506 may have an environmental parameter output 512. The signal generator 514, the signal detector 516 and the parameter calculation module 506 may be included in a controller or signal processing unit 500. The environmental parameter sensor 4000 may detect an acoustic signal from a detected output 508 produced from the second microphone 502. The environmental parameter sensor 4000 may detect a delayed version of the acoustic signal from a detected output 510 produced from the first microphone 108. The second microphone 502 may be located a known distance from the first microphone 108. The environmental parameter sensor 4000 may determine the value of one or more environmental parameters such as ambient air temperature, relative humidity and wind speed from amplitude and/or delay differences between the acoustic signal and the delayed acoustic signal.

When incorporated into a mobile device such as a smart phone, the first microphone 108 of environmental parameter sensor 4000 may also be used for voice recording and placed at a top edge of the smart phone, the second microphone 502 may also be used for voice calls and be placed at the bottom edge of the smart phone. The detected signal from the second microphone 502 may be relatively close to the loudspeaker 106 and so considered to be the reference signal. The parameter calculation module 506 may for example determine a temperature reading from the phase difference between the reference signal and the delayed signal, since the phase difference may correspond to the time of flight of an acoustic signal between the second microphone 502 and the first microphone 108. The environmental parameter sensor 4000 may be implemented using some shared components such as microphones and speakers and so provide an environmental parameter sensor at reduced cost. Alternatively other acoustic transducers may be used instead of a microphone and a speaker.

Figure 9:
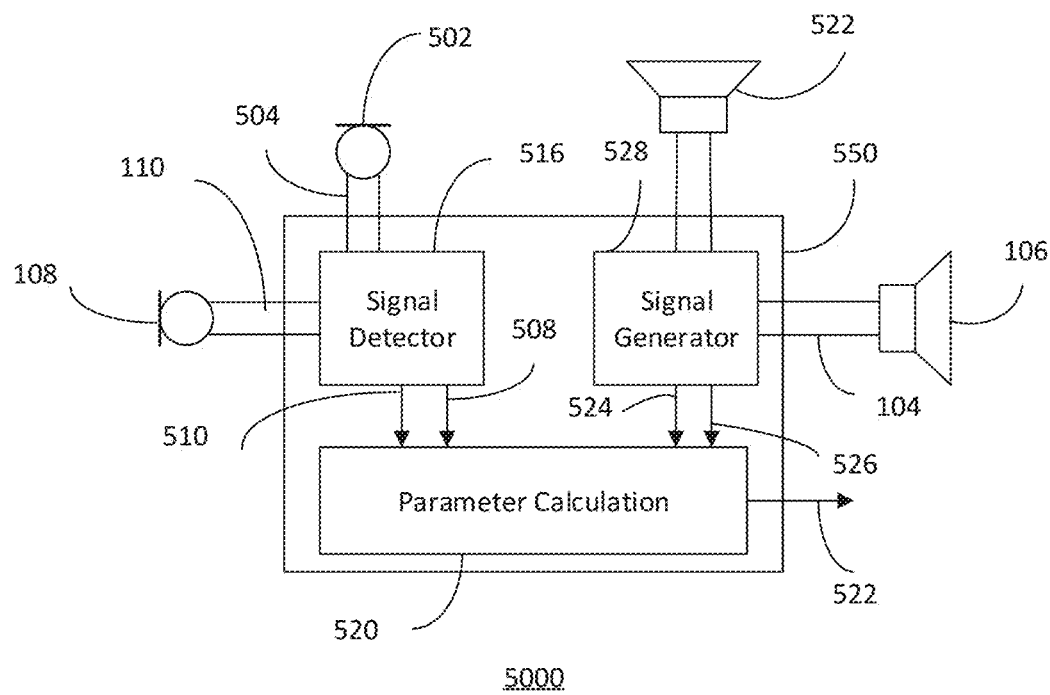
FIG. 9 illustrates an environmental parameter sensor according to an embodiment.

FIG. 9 shows an environmental parameter sensor 5000. A signal generator 528 may generate an acoustic signal waveform. An output 104 of the signal generator 528 may be connected to a loudspeaker 106. A further output 530 of the signal generator 528 may be connected to a second loudspeaker 522. The signal generator may have outputs 524,526 connected to parameter calculation module 520. A signal detector 516 may have an input 110 connected to a microphone 108. The signal detector 516 may have a second input 504 connected to a second microphone 502. The signal detector 516 may have a first detector output 508 connected to the parameter calculation module 520. The signal detector 516 may have a second detector output 510 connected to the parameter calculation module 520. The parameter calculation module 520 may have an environmental parameter value output 522. The signal generator 528, the signal detector 516 and the parameter calculation module 520 may be included in a controller or signal processing unit 550.

In operation, the environmental parameter sensor 5000 may emit a first signal from loudspeaker 106 generated by signal generator 514. A reference signal corresponding to the first emitted acoustic signal may be routed to the parameter calculation module 520 on signal generator output 524. A second acoustic signal may be emitted from second loudspeaker 522 generated by the signal generator 528. A second reference signal corresponding to the second acoustic emitted signal may be routed to the parameter calculation module 520 on signal generator output 526. The first emitted acoustic signal may be detected by first microphone 108 and the detected delayed signal may be routed to the parameter calculation module 520 on the signal detector output 508. The second emitted acoustic signal may be detected by the second microphone 502 and the corresponding detected delayed signal may be routed to the parameter calculation module 520 on the second signal detector output 510.

The environmental parameter sensor 5000 may determine the value of one or more environmental parameters such as ambient air temperature, relative humidity and wind speed from amplitude and/or phase differences between the reference signal and the delayed signal and from amplitude and/or phase differences between the second reference signal and the second delayed signal. By using multiple speaker microphone pairs for measurement, the accuracy of the determined environmental parameter may be improved for example by averaging the determined values.

When incorporated into a mobile device such as a smart phone, the first microphone 108 of environmental parameter sensor 5000 may also be used for voice recording and placed at a top edge of the smart phone, the second microphone 502 may also be used for voice calls and be placed at the bottom edge of the smart phone. The detected signal from the second microphone 502 may be relatively close to the loudspeaker 106 which may be used for playing music. The second loudspeaker 522 may be used as a receiver speaker for voice calls and located relatively close to the first microphone 108. Consequently the first detected signal may be received from a signal emitted in the opposite direction to the second detected signal. The parameter calculation module 520 may determine a wind speed from a difference in the measured speed of sound in each of the directions.

Figure 10:
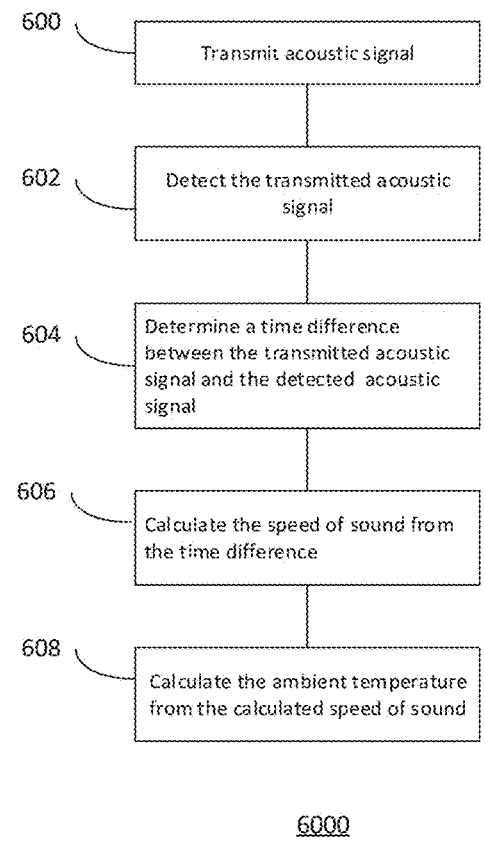
FIG. 10 shows a method of temperature sensing according to an embodiment.

FIG. 10 describes a method of determining an ambient temperature 6000. In step 600 an acoustic signal waveform may be generated for transmitting via an acoustic transducer such as a loudspeaker. In step 602, an acoustic signal transmitted by a loudspeaker may be detected via a second acoustic transducer such as a microphone. In step 604 a time difference may be determined between the transmitted acoustic signal and the detected acoustic signal. In step 606 a measurement of the speed of sound may be determined from the time difference between the transmitted acoustic signal and the detected acoustic signal. In step 608 the ambient temperature may be determined from the calculated speed of sound. It will be appreciated that the measured time difference or time of flight of the acoustic signal between the acoustic transducers for a given distance is inversely proportional to the speed of sound. Consequently the ambient temperature may be determined from the time of flight value without an explicit intermediate step to calculate a value for the speed of sound.

Figure 11:
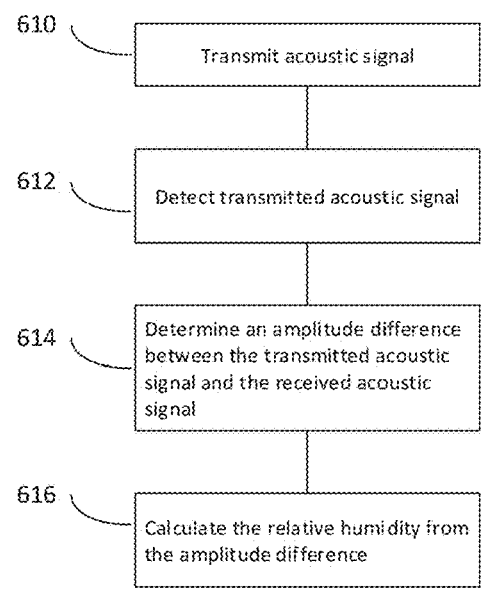
FIG. 11 shows a method of relative humidity sensing according to an embodiment.

FIG. 11 describes a method of determining the relative humidity 7000. In step 610 acoustic signal waveform may be generated for transmitting via an acoustic transducer such as a loudspeaker. In step 612 an acoustic signal transmitted by a loudspeaker may be detected via a second acoustic transducer such as a microphone. In step 614 an amplitude difference between the transmitted acoustic signal and the received acoustic signal may be determined. In step 616 the relative humidity may be determined from the amplitude difference. The amplitude difference may be determined for example by means of a lookup table containing the pre-characterised relationship between the attenuation of the transmitted reference signal through the air and the relative humidity.

Figure 12:
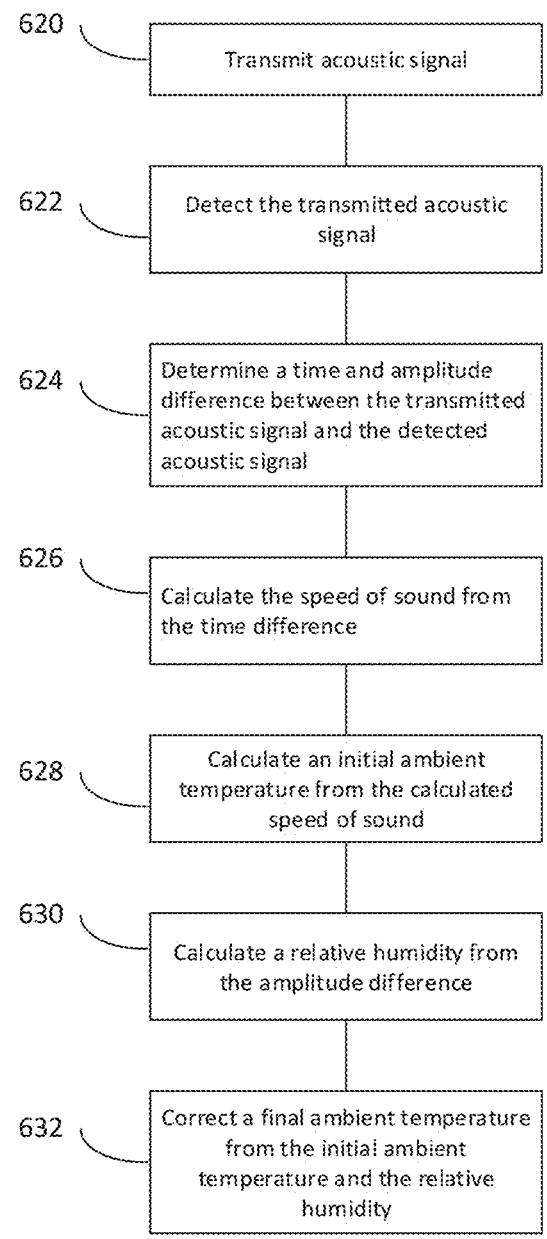
FIG. 12 shows a method of temperature sensing corrected for relative humidity according to an embodiment.

FIG. 12 describes a further method of determining an ambient temperature 8000. In step 620 an acoustic signal may be transmitted via the loudspeaker or other acoustic output transducer. In step 622 an emitted acoustic signal may be detected via a microphone or other input acoustic transducer. In step 624 a time delay and amplitude difference between the transmitted acoustic signal and the detected acoustic signal may be determined. In step 626 a value of the speed of sound may be determined from the time difference between transmitted acoustic signal and the detected acoustic signal. In step 628 an initial ambient temperature may be determined from the calculated speed of sound. In step 630 a relative humidity value may be determined from the amplitude difference between the transmitted acoustic signal and the detected acoustic signal. In step 632 a corrected final ambient temperature may be determined from the initial ambient temperature and the relative humidity.

Figure 13:
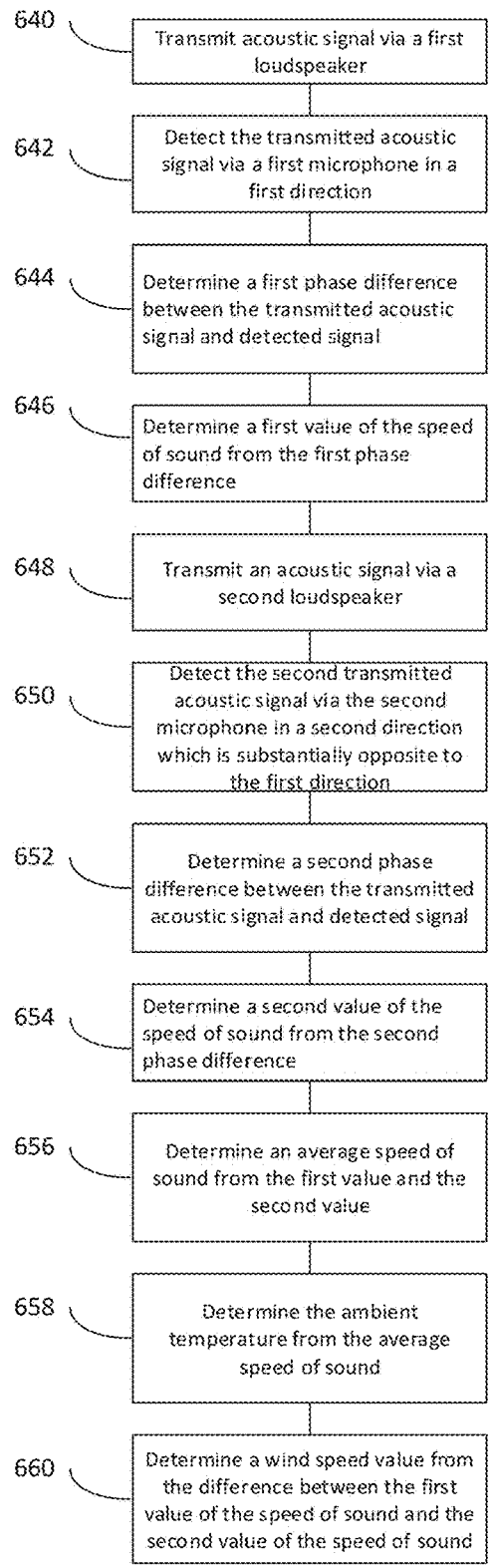
FIG. 13 shows a method of detecting wind speed and a method of temperature sensing corrected for wind speed according to an embodiment.

FIG. 13 describes a method of determining at least one environmental parameter 9000. In step 640 an acoustic signal may be transmitted via a first loudspeaker. In step 642 the transmitted acoustic signal may be detected by a first microphone in a first direction. In step 644 a first phase difference, corresponding to a time delay, may be determined between the transmitted acoustic signal and the detected signal. In step 646 a first value of the speed of sound may be determined from the first phase difference. In step 648 a second acoustic signal may be transmitted via the second loudspeaker. In step 650 the second transmitted acoustic signal may be detected by the second microphone in a second direction which is substantially opposite to the first direction. Substantially opposite may be considered as equivalent to a rotation within the range of 170 to 190 degrees. In step 652 a second phase difference may be determined between the transmitted acoustic signal and a second detected signal. In step 654 a second value of the speed of sound may be determined from the second phase difference. In step 656, an average value of the speed of sound may be determined from the first speed of sound value and the second speed of sound value. In step 658 an ambient temperature value may be determined from the average value speed of sound. In step 660 a wind speed value may be determined from the difference between the first value of the speed of sound and the second value of the speed of sound.

Figure 14:
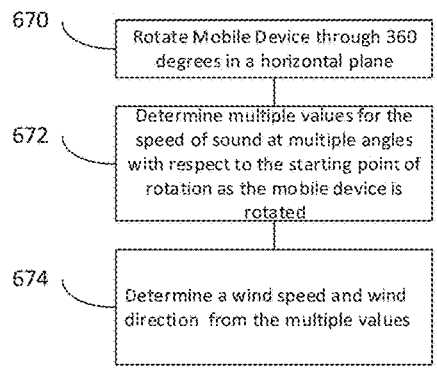
FIG. 14 illustrates a method of determining wind speed and wind direction in a mobile device according to an embodiment.

FIG. 14 describes a method of determining a wind speed and wind direction 10000 in a mobile device such as a smart phone including an embodiment of the environmental parameter sensor and an orientation sensor. In step 670, the mobile device may be rotated through 360° in a horizontal plane. In step 672 multiple values speed of sound may be determined at multiple angles with respect to the starting point of rotation, as the mobile device is rotated. The angle values may be detected by an electronic compass or a gyroscope provided within the same mobile device. In step 674 a wind speed and wind direction may be determined from the multiple values.

Figure 15:
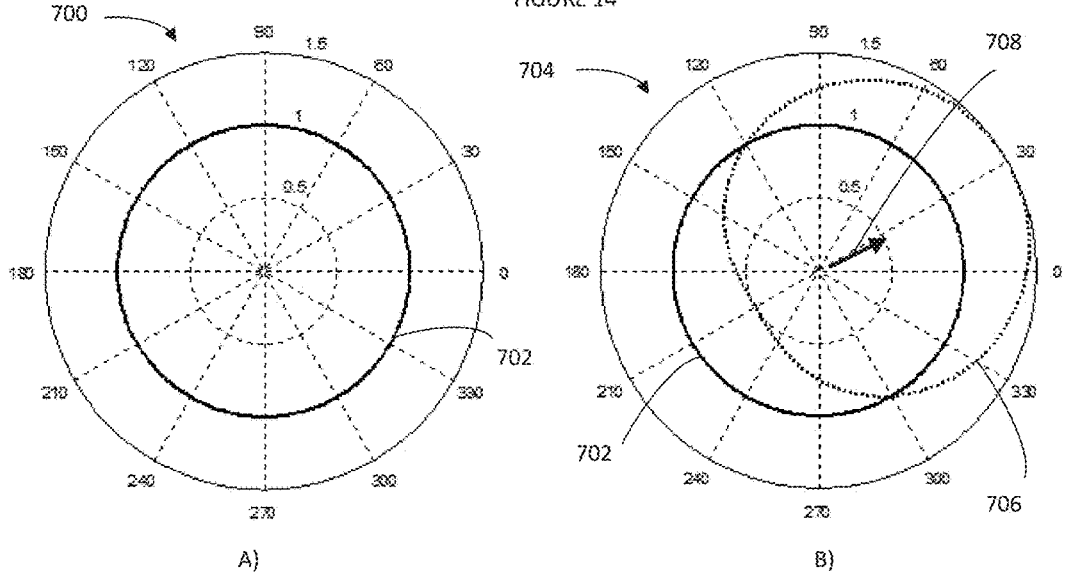
FIG. 15 shows a) a polar plot of speed of sound measured in calm air and b) a polar plot in windy conditions which may be used to determine wind speed and wind direction in the method of FIG. 14.

FIG. 15 illustrates a) polar plot 700 in calm air, and b) a polar plot 704 in windy conditions. During the rotation, measurements are continuously performed. In calm air, the speed of sound in all directions should be the same and if plotted in a polar plot 700, all measurement points make a circle where the radius of the circle indicates the speed of sound as shown in 702. In windy conditions, the circle is displaced 706 towards the wind direction and deformed by the wind vector 708, as shown in polar plot 704. The wind vector 708 may be determined from the orientation of the displaced curve 706, from which a value of the wind direction and wind speed can also be determined. Thus this method can also be used as an acoustic 2D anemometer. In addition, a feature of the displaced curve 706 is that all chords that cross the origin have the same length, which is 2 times the speed of sound in calm air c0. By calculating the length of the chords, the speed of sound in calm air may be obtained from which, for example, air temperature may be determined as herein described.

Figure 16:
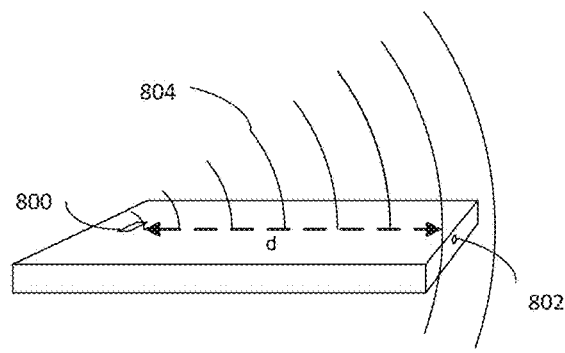
FIG. 16 shows a mobile phone including an environmental parameter sensor according to an embodiment.

FIG. 16 illustrates an example mobile phone 11000 including an environmental parameter sensor. The mobile phone 11000 may have a speaker 800 and a microphone 802 arranged at a fixed distance d apart. To determine an environmental parameter a controller or processing unit (not shown) may generate an acoustic signal waveform which is then transmitted through the speaker 800. The transmitted acoustic signal 804 may be received by the microphone 802 coupled to the controller (not shown). The controller may determine a delay between the transmission and reception of the acoustic signal 804 corresponding to a time-of-flight of the acoustic signal between the speaker 800 and microphone 802. The distance d between the microphone 802 and the speaker 800 is fixed and predetermined, so consequently a value for the speed of sound in air may be determined from the time-of-flight value. A value of ambient temperature may be determined from the speed of sound value. The controller in the mobile phone 11000 may determine an attenuation of the acoustic signal 804 over the distance d from the amplitude difference between the transmitted acoustic signal waveform and the received acoustic signal waveform. The distance d between the microphone 802 and the speaker 800 is fixed and predetermined, so a value of relative humidity may be determined from the attenuation of the acoustic signal 804.

Figure 17:
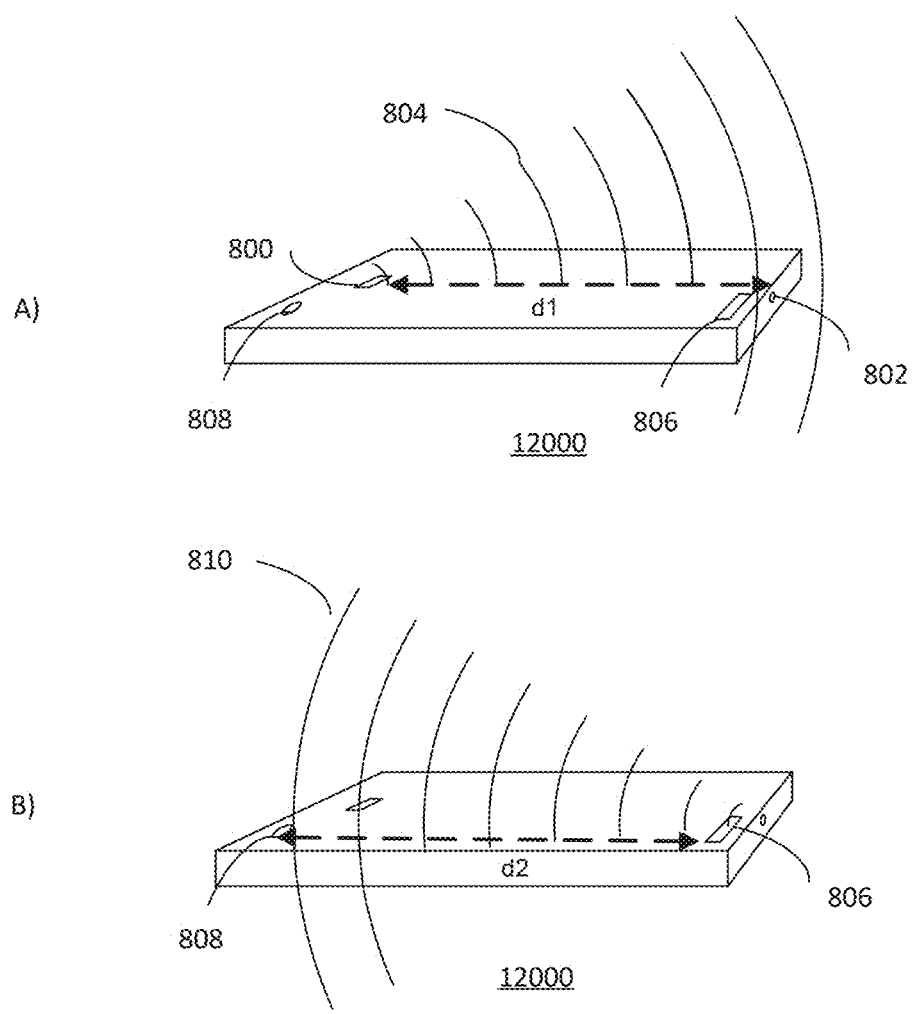
FIG. 17 illustrates a mobile phone including an environmental parameter sensor according to an embodiment a) during a first measurement and b) during a second measurement.

FIG. 17 illustrates an example mobile phone 12000 including an environmental parameter sensor. The mobile phone 12000 may have a speaker 800 and a microphone 802 arranged at a fixed distance d1 apart. The mobile phone may have a further speaker 806 and a further microphone 808 arranged a distance d2 apart. The speaker 800 and the further microphone 808 may be located near a first edge of the mobile phone 12000. The microphone 802 and the further speaker 806 may be located near a second opposite edge of the mobile phone 12000. To determine an environmental parameter a controller or processing unit (not shown) may generate an acoustic signal waveform which is then transmitted through the speaker 800. The transmitted acoustic signal 804 may be received by the microphone 802 coupled to the controller (not shown). The controller may determine a delay between the transmission and reception of the acoustic signal 804 corresponding to a time-of-flight of the acoustic signal between the speaker 800 and microphone 802. The distance d1 between the microphone 802 and the speaker 800 may be fixed and predetermined, so consequently a first value for the speed of sound in air may be determined from the first time-of-flight value. A first value of ambient temperature may be determined from the speed of sound value. A further acoustic signal waveform may be transmitted through the further speaker 806. The further transmitted acoustic signal 810 may be detected by the further microphone 808. The controller may determine a delay between the transmission and reception of the acoustic signal 810 corresponding to a time-of-flight of the acoustic signal between the further speaker 806 and the further microphone 808 due to acoustic signal 810. The distance d2 between the microphone 802 and the speaker 800 may be fixed and predetermined, so consequently a second value for the speed of sound in air may be determined from the second time-of-flight value. As the first time of flight value was determined in an orientation substantially opposite to the second orientation, the ambient temperature value may be averaged to compensate for the effect of wind speed in the direction of the measurement.

In a further example, an active headset including one or more of the example environmental parameter sensors described herein may transmit a reference signal which may be an ultrasound signal or other non-audible signal that may be superimposed on a sound signal for example music. The ultrasound signal may be detected at a microphone which may be arranged at a fixed distance with respect to the earpiece. The microphone may be located for example on a rigid holder or located on the bridge between the earpieces. Many headsets have a small aperture to the outside air to equalize the pressure in the loudspeaker, so that that higher frequency tones may be emitted into the ambient environment and detected by the microphone. In this way an environmental parameter such as ambient air temperature may be measured while for example simultaneously listening to music.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub combination.

The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several

The invention claimed is:

1. An environmental parameter sensor for a mobile device comprising:
   a first acoustic transducer having a first sound signal input;
   a second acoustic transducer having a second sound signal input and arranged at a fixed distance from the first acoustic transducer; and
   a controller circuit coupled to the first acoustic transducer and the second acoustic transducer;
   wherein the controller circuit is
      for determining at least one of a time-of-flight value and an attenuation value of an acoustic signal between the first acoustic transducer and the second acoustic transducer using the first and second sound signal inputs and
      for determining at least one environmental parameter from the at least one of the time-of-flight value and the attenuation value;
   wherein the controller circuit is further for determining a further time of flight value of the acoustic signal between the first acoustic transducer and the second acoustic transducer using the first and second sound signal inputs;
   wherein the at least one environmental parameter comprises a wind speed value; and
   wherein the controller circuit is further for determining the wind speed value from a difference between the time of flight value and the further time of flight value.

2. The environmental parameter sensor of claim 1 wherein the controller circuit is further:
   for generating an acoustic signal waveform for transmission via the first acoustic transducer;
   for detecting the transmitted acoustic signal received via the second acoustic transducer; and
   for determining at least one of a time-of-flight value and an attenuation value of the acoustic signal from at least one of a time difference and an amplitude difference between the transmitted acoustic signal waveform and the received acoustic signal waveform.

3. The environmental parameter sensor of claim 1 wherein the controller circuit is further
   to detect a first acoustic signal waveform via the first transducer and
   to detect a second acoustic signal waveform via the second acoustic transducer and
   for determining the at least one of a time-of-flight value and an attenuation value of an acoustic signal from at least one of a time difference and an amplitude difference between the first acoustic signal waveform and the second acoustic signal waveform.

4. The environmental parameter sensor of claim 1 wherein the controller circuit is further
   for determining a value the speed of sound from the determined time of flight value and
   for determining the at least one environmental parameter from the speed of sound value and wherein the at least one environmental parameter comprises temperature.

5. The environmental parameter sensor of claim 1 wherein the controller circuit further comprises
   an acoustic signal waveform generator coupled to the first acoustic transducer,
   a signal detector coupled to at least one of the first acoustic transducer and the second acoustic transducer, and
   a parameter calculation circuit coupled to at least one of the signal detector and the acoustic signal waveform signal generator.

6. The environmental parameter sensor of claim 5
   wherein the parameter calculation circuit further comprises a delay calculation circuit;
   wherein the delay calculation circuit is operable to determine a time difference value between the acoustic signal waveform detected or emitted via the first acoustic transducer and the acoustic signal waveform detected via the second acoustic transducer.

7. The environmental parameter sensor of claim 6
   wherein the delay calculation circuit comprises a cross-correlator.

8. The environmental parameter sensor of claim 5 wherein the parameter calculation circuit further comprises an amplitude comparator and wherein the acoustic signal waveform comprises a first reference frequency and a second reference frequency and the controller circuit is operable to determine the at least one environmental parameter from the attenuation of the acoustic signal and wherein the at least one environmental parameter comprises the relative humidity.

9. The environmental parameter sensor of claim 1:
   wherein the controller circuit is further for determining the time of flight value in a first orientation of the environmental parameter sensor and the further time of flight value in a further orientation of the environmental parameter sensor.

10. The environmental parameter sensor of claim 1:
    wherein the controller circuit is further for determining a compensated temperature value in dependence of the wind speed value.

11. The environmental parameter sensor of claim 1 is at least one of a temperature sensor, a wind speed sensor, and a relative humidity sensor.

12. An environmental parameter sensor for a mobile device comprising:
    a first acoustic transducer;
    a second acoustic transducer arranged at a fixed distance from the first acoustic transducer; and
    a controller circuit coupled to the first acoustic transducer and the second acoustic transducer;
    wherein the controller circuit is
       for determining at least one of a time-of-flight value and an attenuation value of an acoustic signal between the first acoustic transducer and the second acoustic transducer; and
       for determining at least one environmental parameter from the at least one of the time-of-flight value and the attenuation value;
    wherein the controller circuit further comprises,
       an acoustic signal waveform generator coupled to the first acoustic transducer;
       a signal detector coupled to at least one of the first acoustic transducer and the second acoustic transducer; and
       a parameter calculation circuit coupled to at least one of the signal detector and the acoustic signal waveform signal generator;
    wherein the parameter calculation circuit further comprises an amplitude comparator;
    wherein the acoustic signal waveform comprises a first reference frequency and a second reference frequency;
    wherein the controller circuit is operable to determine the at least one environmental parameter from the attenuation of the acoustic signal; and wherein the at least one environmental parameter comprises a relative humidity.

13. An environmental parameter sensor for a mobile device, comprising:
- a first acoustic transducer;
- a second acoustic transducer;
- a third acoustic transducer;
- a fourth acoustic transducer;
- wherein the first and second transducers are coupled together in a first orientation and are separated by a first distance;
- wherein the third and fourth transducers are coupled together in a second orientation and are separated by a second distance;
- a controller circuit coupled to the first, second, third and fourth transducers and,
  - for determining a first time-of-flight value and/or first attenuation value of a first acoustic signal between the first and second transducers;
  - for determining a second time-of-flight value and/or second attenuation value of a second acoustic signal between the third and fourth transducers; and
  - for determining an environmental parameter from an average of the first and second time-of-flight values and/or the first and second attenuation values; and
- a signal detector coupled to at least one of the first acoustic transducer and the second acoustic transducer.

14. The environmental parameter sensor of claim 13:
wherein the first orientation and the second orientation are substantially opposite.

15. The environmental parameter sensor of claim 13:
wherein the environmental parameter is an ambient temperature.

* * * * *